United States Patent [19]

Ingberg et al.

[11] Patent Number: 5,008,388
[45] Date of Patent: Apr. 16, 1991

[54] PROCESS FOR PREPARATION OF A NEW HEMIN COMPLEX

[75] Inventors: Grels D. Ingberg, Ekenäs; Ritva L. A. Penttilä, Helsinki; Reino O. Tokola, Helsinki; Raimo Tenhunen, Helsinki, all of Finland

[73] Assignee: Huhtamäki Oy, Turku, Finland

[21] Appl. No.: 803,630

[22] Filed: Dec. 2, 1985

Related U.S. Application Data

[63] Continuation-in-part of Ser. No. 636,860, Aug. 1, 1984, abandoned.

[30] Foreign Application Priority Data

Aug. 10, 1983 [FI] Finland .................. 832870

[51] Int. Cl.$^5$ .................. C07B 47/00; C07K 3/00
[52] U.S. Cl. .................. 540/145; 530/400
[58] Field of Search .................. 514/185, 6; 540/145; 530/400

[56] References Cited

U.S. PATENT DOCUMENTS 4,431,581  2/1984  Lindroos .................. 530/385

FOREIGN PATENT DOCUMENTS

81/02834  10/1981  PCT Int'l Appl. .

OTHER PUBLICATIONS

Wakid N. W. & Helou K. Y.: Int. J. Biochem. 4: 259–267, 1973.
Yamagishi et al., Chem. Abstracts, vol. 96:64451n (1982).
Livshits et al., Chem. Abstracts, vol. 87:53549p (1977).
Nanzyo et al. *J. Biol. Chem.*, pp. 3431–3440, vol. 243, No. 12, 1968.

*Primary Examiner*—Jacqueline Stone
*Attorney, Agent, or Firm*—McAulay Fisher Nissen Goldberg & Kiel

[57] ABSTRACT

The present invention relates to a method for the preparation of a new, physiologically active, water-soluble complex compound, hemin arginate or hemin lysinate. According to the invention crystalline hemin and one of the amino acids L-arginine or L-lysine, in a molar proportion of 1:3, are allowed to react at room temperature under vigorous stirring for 10 to 15 hours in a solvent mixture of acetone and water in a ratio of 300:20 v/v. The hemin arginate or hemin lysinate thus formed is a powdery, stable compound suitable for use as raw material in tablets or capsules or as dry substance for preparation of injections for treatment of various types of anemia, including iron deficiency anemia and anemias and diseases associated with defects in heme synthesis.

7 Claims, No Drawings

PROCESS FOR PREPARATION OF A NEW HEMIN COMPLEX

CROSS REFERENCE TO RELATED APPLICATION

This application is a continuation-in-part of prior copending application Ser. No. 636,860, filed Aug. 1, 1984, by Grels Daniel Ingberg, Ritva Laila Aneri Penttila, Reino Olavi Tokola, and Raimo Tenhunen for "Process for Preparation of a New Hemin Complex and Product Produced by Process," assigned to the same assignee as the present invention, now abandoned.

BACKGROUND OF THE INVENTION

The present invention relates to a method for the preparation of a physiologically active, water-soluble hemin arginate or hemin lysinate complex intended for use in tablets or capsules or as a dry substance for injection after reconstitution, e.g., with sterile saline solution.

Hemin occurs in organisms as a prosthetic group of hemoglobin in most cytochromes and in certain enzymes. Hemoglobin is synthesized in the bone marrow. When hemin proteins decompose, hemin is released, but only a minor part of it is used in the synthesis of new hemin proteins under normal physiological conditions. Hemin is split by the action of hemin oxygenase into biliverdin, which is further reduced to bilirubin. Native, intact hemoglobin does not, naturally, serve as a substrate for hemin oxygenase.

Defects in the hemoglobin synthesis may be due to disturbed synthesis of hemin or of globin chains. The hemin synthesis may be disturbed because of: (a) lack of some component necessary for the synthesis, or (b) dysfunction of an enzyme catalyzing the synthesis.

Iron deficiency is the limiting factor in the hemin synthesis. The organism gets its daily requirement of iron (1–2 mg) with food. Iron deficiency may be due to a diet deficient in iron or possibly to the presence of iron-building compounds in the food. Disturbances in the iron absorption mechanism may also lead to iron deficiency, despite adequate iron content in the food. Regardless of the cause, iron deficiency sooner or later leads to anemia.

In the rarely occurring vitamin $B_6$ deficiency, the absorption of iron is normal, but its utilization by the cells is inhibited. As a consequence of this, a certain type of sideroblastic anemia develops. Iron deficiency anemia is treated either with oral iron preparations, e.g., iron sulphate or iron gluconate, or, more rarely, with injections such as iron sorbitol. When the iron absorption mechanism is disturbed, these conventional oral preparations are useless; the iron does not even penetrate into the cells of the intestinal mucosa. In contrast to inorganic iron, hemin iron, in which the iron is bound to hemin, is absorbed by these cells even in such cases of disturbed iron absorption which are resistant to conventional oral therapy. Thus, hemin iron is the only known, effective remedy for oral treatment of therapy-resistant cases. Hemin iron has been found to be four to five times better absorbed than inorganic iron, even in quite healthy subjects (Seppanen H & Takkunen H: Suomen Laakarilehti 36:2071–2072, 1981).

The synthesis of hemin is enzymatically regulated. Impaired function of the enzymes catalyzing the hemin synthesis may be either hereditary or due to external factors. It invariably leads to decreased formation of hemin, manifested by the development of porphyria or certain kinds of sideroblastic anemia or other diseases.

Porphyria is the most important group of diseases resulting from impaired enzyme function. In porphyria patients there is an accumulation of porphyrins, intermediary products in the hemin synthesis, and an increased excretion of these into urine and feces. Most kinds of porphyria are manifested by acute attacks which are extremely difficult to master.

Sometimes, sideroblastic anemias of different kinds may develop instead of porphyria as a consequence of dysfunction of enzymes participating in the hemin synthesis. Sideroblastic anemias, too, may be either hereditary or acquired.

The treatment of porphyria has until now been based principally on the avoidance of certain drugs and the administration of large amounts of carbon hydrates during the acute attacks, but the effect has been poor. Since the etiology of porphyria became clarified, intravenous treatment with hemin compounds (hematin) has been continuously gaining ground. Hematin has proved effective in the treatment of porphyria attacks, but in more than 50% of the patients it has caused thrombophlebitis. Moreover, it is very unstable and therefore unsuitable for production on an industrial scale. There are, thus, very few possibilities for effective treatment of porphyria patients.

The aim of the present invention is to produce a water-soluble hemin iron compound for treatment of certain kinds of anemia, with the iron ready at hand, so to speak, in the hemin molecule. The compound is intended, in the first place, for treatment of porphyria, where the normal production of hemoglobin is disturbed for some reason or other. As the compound is intended for oral administration in tablets or capsules as well as for injection, it must be water-soluble.

Hemin, which is sparingly soluble in water, can be obtained in pure form from blood by extraction with a mixture of hydrochloric or acetic acid from a water solution of hemolyzing erythrocytes. Another method is based on the extraction of hemin with acetone in the presence of, e.g., histidylhistidine, pilocarpine, or imidazole at pH 7.0 (Wakid N. W. & Helou K. Y.: Int. J. Biochem. 4:259–267, 1973).

PCT patent application Ser. No. 813749 (PCT/FI81/00026) describes a method for the preparation of a water-soluble hemin concentrate in which about 40% w/w is hemin and the rest is a "blood substance" of unknown nature. The product is intended for use in lyophilized form as an iron supplement in food or as an antianemic drug.

The drawback of this method is that the final product is a mixture of hemin and "blood substance." As the latter component is not uniform, the mixture is unsuitable for injection.

The above-referenced PCT patent application corresponds to U.S. Pat. No. 4,431,581, Lindroos, issued Feb. 15, 1984. Not only are the products of this Lindroos patent not intended for injection purposes, as are the water-soluble materials of the present invention, but the materials of the Lindroos patent could not be used for injection purposes because of the high risk of life threatening anaphylactic shock, if an attempt were made to use them as injectable materials. Nothing set forth in the Lindroos patent would indicate that they are useful for such purposes, and, in fact, a review of the process conditions employed in Lindroos and analytical testing of the product indicates that the products of Lindroos are totally different from the products of the present invention. For example, Lindroos operates at a high pH, where heme easily degrades; in accordance with the present invention, reaction is carried out in the presence of amino acids which are weakly basic.

A sample of the Lindroos product, in accordance with U. S. Pat. No. 4,431,581 was acquired from a licensee of a corresponding patent. The iron content of the heme concentrate of Lindroos was found to be 2.94%, while a product made in accordance with the present invention had an iron content of 4.74%. Still further, the iron of the Lindroos patent in the heme concentrate is in the +2 oxidation state, while the iron in the material of the present invention is in the +3 oxidation state. A measurement of the pH of a 1% water solution of the Lindroos patent was found to be 8.78, while a similar test carried out on the product of the present invention, hemin arginate, in a 1% water solution was found to be 8.55. Of further significance, spectra were run of both the Lindroos product and the hemin arginate product of the present invention by infrared, ultraviolet, and hydrogen nmr. A comparison of the nmr spectra of the two products clearly shows two totally different products, a comparison confirmed by a study of the ultraviolet and infrared spectra.

A comparison was also made between the product of the present invention and that described in Livshits et al, Zh.Org.Khim 1977, 13(2), page 436 (Chem. Abstracts Vol. 87:53549 p. 1977). A comparison of the spectra shown in FIG. 2b on page 440 of the referenced Livshits article with the spectra described above for the material of the present invention showed two completely different products. Further, Livshits et al describes the synthesis of amides where the carboxylic acid groups of heme, via normal methods for peptide synthesis, have been coupled to lysine and some derivatives of this amino acid so that a strong covalent bond is formed. To precipitate heme from this compound, hydrolysis is required, which can be accomplished either enzymatically or by boiling for several hours in strong acid solution. By contrast, the present invention describes a complex salt of heme and amino acid where the binding is electrovalent, so that it has been shown that heme may be precipitated merely by acidifying a solution of the product.

Porphyria has been treated in hospitals with a mixture prepared extempore by dissolving hemin in a sterile sodium carbonate solution (hematin). As this solution is unstable it cannot be manufactured as a commercial product on a large scale. Moreover, hematin causes thrombophlebitis at the site of injection in about 50% of the cases, probably because of the high pH of the solution. This is a serious drawback which reduces the usefulness of the product considerably.

DESCRIPTION OF THE INVENTION

The present invention relates to a method of preparing a water-soluble hemin complex by allowing sparingly water-soluble, crystalline hemin to react with a suitable base, e.g. an amino acid such as L-lysine or L-arginine, in a solvent mixture containing, e.g., water and acetone. The composition of the solvent, i.e. the proportion of organic solvent to water, is surprisingly important for the medical value of the final product. The water content in the solvent mixture is so low, about 7%, that neither hemin nor the fairly readily soluble L-arginine is dissolved. The reaction takes place under vigorous stirring and the pH of the solution is continuously controlled. The product formed is separated and dried; the hemin compound is thus obtained in dry form and is soluble in water, which is essential from the medical as well as the pharmacotechnical point of view.

The present invention also relates to the water soluble complex of hemin and either L-arginine or L-lysine, where the molar proportion of hemin to the amino acid is from 1:1 to 1:4. Preferably, the molar ratio of hemin to L-arginine is 1:2 to 1:4, most preferably 1:3, while the preferred ratio of hemin to L-lysine is from 1:3 to 1:4, most preferably 1:3. Further, the invention relates to compositions containing these complexes, either in injection or in tablet form.

While not wishing to be bound by theory, it is believed that the hemin molecule contains two carboxyl groups which react with the basic amino groups of L-lysine or L-arginine. In particular, with the L-arginine, it is believed that it stabilizes the heme in solution, partly forming salt bridges between the porphyrin carboxyls and the guanidino groups in the arginine, in part, by buffering the pH of the solution to about 9. It is not certain whether the carboxyl or guanidine groups of the arginine function has ligands for the heme iron, but it is a distinct possibility.

Hemin arginate and hemin lysinate prepared according to the invention were dissolved in water, and the pH of the solution was measured and compared at different time points with the pH of a mechanical mixture of hemin and L-arginine dissolved in water. The results are seen in Table 1.

TABLE 1

| Material | Concentration Hemin Complex/ Water | pH 0 Min. | pH 60 Min. | pH 24 h |
| --- | --- | --- | --- | --- |
| Hemin arginate | 0.02937 g/25 ml | 8.22 | 8.22 | 8.22 |
| Hemin lysinate | 0.02760 g/25 ml | 8.10 | 7.97 | 8.13 |
| Hemin + L-arginine | 0.01630 g/25 ml 0.01307 g/25 ml | 10.13 | 9.81 | 9.33 |

The pH measurements of Table 1 show that the pH of the hemin arginate and hemin lysinate is stable (pH about 8) for up to 24 hours. The pH of the mechanical mixture, on the other hand, decreases very slowly, probably owing to the extremely slow reaction between the carboxyls in the hemin and the amino group in the L-amino acid. A therapeutically useful product cannot therefore be obtained by this method. Hemin arginate and hemin lysinate prepared according to the invention consist of a complex compound where the L-amino acid has reacted with the hemin carboxyls.

To determine, on the one hand, the optimal molar relation between the two reactants and, on the other, the most suitable composition of the solvent mixture, the tests set forth below were performed with hemin and arginine.

Crystalline hemin and L-arginine in molar proportions of 1:2 and 1:3 were allowed to react, under vigorous stirring, in a solvent mixture consisting of an organic solvent and water in varying proportions. The precipitates formed were filtered off, washed and dried.

The solubility in water was determined by dissolving, under vigorous stirring for about one hour, about 1.0 g of the hemin arginate complex obtained in each test in 50 ml. of distilled water.

The solutions were centrifuged (about 3500 rev./min.) and the residue was washed with 10 ml. of distilled water and 10 ml. of acetone, after which it was dried and weighed. The insoluble residue consisted mainly of unreacted hemin. The test results are presented in Table 2.

TABLE 2

| Hemin:L-arginine | | | Amt. of | | |
|---|---|---|---|---|---|
| Weights (g) | Molar Proportion | Solvent | Solvent (ml.) | Temp. °C. | Insoluble Residue |
| 6.52:3.48 | 1:2 | methanol | 300 | 20 | tar |
| 6.52:3.48 | 1:2 | ethanol | 300 | 20 | ≈100% |
| 6.52:5.22 | 1:3 | " | 300 | 40 | 20.2% |
| 6.52:3.48 | 1:2 | isopropanol | 300 | 20 | ≈100% |
| 6.52:3.48 | 1:2 | isopropanol/water | 300:20 | 20 | 21.2% |
| 6.52:5.22 | 1:3 | isopropanol/water | 300:20 | 20 | 9.7% |
| 6.52:3.48 | 1:2 | acetone/water | 300:15 | 20 | 16.8% |
| 6.52:3.48 | 1:2 | acetone/water | 300:20 | 20 | 12.4% |
| 6.52:5.22 | 1:3 | acetone/water | 300:10 | 20 | ≈100% |
| 6.52:5.22 | 1:3 | acetone/water | 300:10 | 40 | 11.4% |
| 6.52:5.22 | 1:3 | acetone/water | 300:15 | 20 | 8.3% |
| 6.52:5.22 | 1:3 | acetone/water | 300:20 | 20 | 0.3% |
| 6.52:5.22 | 1:3 | acetone/water | 300:30 | 20 | tar |
| 6.52:5.22 | 1:3 | acetone/water | 150:10 | 20 | 4.2% |
| 6.52:5.22 | 1:3 | acetone/water | 150:12.5 | 20 | tar |

The tarry substance formed in some of the tests could not be transferred into powder form.

The optimum molar proportion of hemin to L-arginine was found to be from 1:2 to 1:4, most preferably 1:3. The most suitable solvent mixture was found to be 300 ml. of acetone and 20 ml. of water.

The local effect of intravenously infused hemin compounds on surrounding tissues was studied by means of infusing 5 mg/kg into the auricular veins of California White rabbits. A conventional hemin carbonate solution (hematin) was used as reference solution. After infusion of hemin arginate solution, the tissue surrounding the vein remained normal, i.e. no sterile inflammation (thrombophlebitis) occurred. A similar result was seen after infusion of a corresponding hemin lysinate solution. Thus, it can be concluded that the compounds do not cause thrombophlebitis when infused intravenously.

When a hemin carbonate solution was administered in the same manner, the tissue surrounding the vein became red and irritated; i.e., a manifest sterile inflammation (thrombophlebitis) developed. Three days after the infusion of the hemin carbonate solution the thrombophlebitis was still manifest.

The physiological character of the different water-soluble hemin compounds was assessed by testing the ability of hemin oxygenase to split the compounds. The physiological substrate for hemin oxygenase, methemalbumin, is split by this into biliverdin, which is further reduced to bilirubin by biliverdin reductase. Thus, the excess hemin which the organism cannot utilize is decomposed, in the first place, by hemin oxygenase into bilirubin and other, closely related substances, which are then normally excreted. The reaction rate limiting enzyme is, thus, hemin oxygenase.

In our enzymatic analyses, performed in order to find out, for one thing, the ability of hemin arginate and hemin lysinate to serve as substrates for hemin oxygenase, the activity of the reference substrate methemalbumin was expressed as 100. The corresponding value obtained for hemin arginate and hemin lysinate was 106. The activities of other hemin amine derivatives, where the amine component was diethanol amine, ethyl amine, cyclohexyl amine, or piperidine, was found to be 13, 21, 31, and 78 respectively. The tests show that hemin arginate and hemin lysinate behave in the organism like normal physiological compounds with regard to hemin oxygenase.

Studies were also carried out by EPR measurements employing a Bruker 200D-SCR instrument, connected to a Bruker data system, ER140. A flow cryostat (ESR-9, Oxford Instruments) was mounted in the spectrometer. A comparison was made of 3.5 mM hemin-arginate complex diluted in different water solutions. This heme concentration corresponds, approximately, to that which would be injected into a patient weighing approximately 80 kg. The EPR spectra of the hemin-arginate complex in saline and in water have axial signals similar to those of a concentrated hemin-arginate complex, i.e., the heme appears to exist in high molecular weight aggregates. In aqueous alcohol solutions, the EPR spectra include additional signals with g-values close to 10 and 3–3.7. It is believed that the dispersing effect of alcohol on heme aggregates is predominantly through reduction of the dielectrical constant of the solvent, and not from coordination to a metal ion. Further, when the hemin-arginate complex is in 4 mM albumin, the EPR spectrum is that of a totally monomeric high spin ferric iron. It has a rhombic signal with g-values of 6.11 and 5.87. The EPR spectrum is very similar to that of hemoglobin, in which heme is specifically bound to the apoprotein.

Similar comparisons were done on a 1.8 mM hemin-arginate complex in aqueous alcohol, in saline, and in 2 mM albumin solution. In the albumin, the absorption spectrum is again very similar to that of hemoglobin with a high Soret maximum at 402 nm and the maxima in the visible at 510, 540, and 620 nm, typical for a high-spin ferric hemoprotein. In aqueous alcohol, the intensity of the Soret band has decreased and the maximum has shifted to 393 nm, whereas the visible spectrum is more diffused with maxima at 490 and 602 nm. In 0.9% sodium chloride, the Soret maximum has decreased further and is shifted to 390 nm, while the spectrum in visible wave lengths shows only a broad band at 600 nm. These absorption spectra corroborate the evidence obtained from EPR spectra that, diluted in human albumin, the hemin-arginate complex is monomeric, in a 40% propyleneglycol - 10% ethanol solution it exists as $\mu$-oxo-dimers and -oligomers, while in a 0.9% sodium chloride or water solution, it exists as higher aggregates. The absorption spectra were measured on a pye-Unicam Model 8002 spectrophotometer in the visible and near-ultraviolet region (350–700 nm), or with a Cary 17 spectrophotometer in the near-infrared region (600–1,400 nm) using 0.1 or 1 mm curettes. The preparation of the products of the present invention is best illustrated by the following examples:

EXAMPLE 1

6.52 g of crystalline hemin (0.01 M) and 3.48 g of crystalline L-arginine (0.02 M) were vigorously stirred for 10 to 15 hours in a beaker provided with a mechanical stirrer and containing a solvent mixture of 300 ml. of acetone and 20 ml. of water. The product formed was filtered off, washed with acetone, and dried.

Yield of hemin arginate: 9.5 g. (95%). Insoluble residue, determined by the method mentioned above: 0.14 g. (1.4%).

EXAMPLE 2

6.52 g. of crystalline hemin (0.01 M) and 4.36 g. of crystalline L-arginine (0.025 M) were treated as described in Example 1.

Yield of hemin arginate: 11.1 g (about 100%). Insoluble residue: 0.042 g (0.42%).

EXAMPLE 3

6.52 g. of crystalline hemin (0.01 M) and 5.23 g. of crystalline L-arginine (0.03 M) were treated as described in Example 1.

Yield of hemin arginate: 12.0 g. (about 102%). Insoluble residue: 0.001 g (0.01%).

EXAMPLE 4

6.52 g. of crystalline hemin (0.01 M) and 6.10 g. of crystalline L-arginine (0.035 M) were treated as described in Example 1.

Yield of hemin arginate: 12.0 g. (95%). Insoluble residue: 0.0005 g (0.005%).

EXAMPLE 5

6.52 g. of crystalline hemin (0.01 M) and 4.39 g. of crystalline L-lysine (0.03 M) were treated as described in Example 1.

Yield of hemin lysinate: 10.8 g. (99%). Insoluble residue: 0.020 g. (0.20%).

It appears that the optimal molar proportion of hemin to arginate is 1:3 (Example 3), because this gave the highest yield of hemin arginate, while the amount of insoluble residue was minimal.

EXAMPLE 6

Male Sprague-Dawley rats (180–250 g) were made porphyric by subcutaneous administration of 300 mg/kg 2-allyl-2-isopropylacetamide (AIA) on three consecutive days. Another group of rats were treated with AIA and with a hemin-L-arginine complex made in accordance with Example 3, 10 mg/kg intraperitoneally on three consecutive days.

In AIA treated rats the daily urinary porphobilinogen (PBG) excretion increased from mean values of 0.08 (range 0.05–0.13) to 6.79 (range 3.91–12.70) $\mu$mol and the daily urinary delta-aminolevulinic acid (ALA) excretion from 0.20 (0.16–0.23) to 7.77 (2.49–11.50) $\mu$mol. In rats treated with AIA and the material made in accordance with Example 3, on the other hand, increases in urinary excretion of PBG (to 0.28, range 0.09–0.45 $\mu$mol/day) and ALA (to 0.51, range 0.23–0.82 $\mu$mol/24 h) were small.

Delta-aminolevulic acid synthase (ALAS) activies in erythrocytes (3.97, range 2.23–6.06 pmol ALA/h/$10^6$ reticulocytes) and livers (15.4, range 12.5–17.1 pmol ALA/mg protein/h) of AIA treated rats were clearly higher than the corresponding values (1.42, range 0.82–1.72 pmol ALA/h/$10^6$ reticulocytes and 11.5, range 9.8–13.7 pmol ALA/mg protein/h) of rats treated with AIA and the material made in accordance with Example 3.

Heme oxygenase (HO) activity decreased in most of the AIA treated rats to a non-measurable level, whereas in rats treated with AIA and the material made in accordance with Example 3, HO activity was 16.2 (range 9.3–29.3) pmol/min/mg protein.

The porphyrinogenic effect of AIA treatment could also be prevented by intramuscular administration of hemin-L-arginine complex made in accordance with Example 3, at doses of 10 mg/kg. A single intravenous injection (20 mg/kg) caused the same antiporphyrinogenic effect.

Studies show that this preparation is at least as effective as the generally used hematin.

EXAMPLE 7

The biochemical effect of a stable and easily soluble heme derivative made in accordance with Example 3 was investigated in ten patients with acute hepatic porphyria in the symptomless phase of the disease. Six patients with actue intermittent porphyria (AIP) received heme 2 mg (two) or 3 mg/kg/day (four) into peripheral veins during four consecutive days. During the treatment mean urinary excretion of porphobilinogen fell from 194 (range 60–465) to 17.2 $\mu$mol/24 h (7.1–30), and that of delta-aminolevulic acid from 133 (range 47–281) to 13.8 $\mu$mol/24 h (8.1–23.4). In four patients with variegate porphyria heme derivative 3 mg/kg/day during four days decreased mean fecal protoporfyin from 650 (range 193–1140) to 89 nmol/g/-day dry weight (62–103) and coproporfyrin from 232 (range 102–360) to 23 nmol/g dry weight (8.5–40).

In two patients with AIP three courses of heme (3 or 4 mg/kg/day for three or four days) were given during acute attack. In a 21-year old woman abdominal symptoms ceased during the second day of treatment on two occasions. In a 43-year old man with abdominal pain and peripheral neuropathy the pain ceased and the neuropathy began to improve after the last of four consecutive infusions.

Thrombophlebitis occurred in none of the porphyric patients during the 51 infusions. No other side-effects or abnormalities in blood chemistry, including coagulation studies, were found. It is concluded that the new heme preparation is safe and effective in the treatment of acute hepatic porphyrias.

EXAMPLE 8

A tablet for oral administration of the hemin arginate of the present invention is given below:

| Material | Amount (mg.) |
| --- | --- |
| Hemin arginate of Example 3 | 386.9 |
| Maize starch | 25.0 |
| Lactose | 50.0 |
| Magnesium stearate | 4.2 |
| Polyvidone | 24.9 |

Weight per tablet 491

The tablet with the composition just referred to is manufactured employing standard tableting procedures.

EXAMPLE 9

A hemin lysinate tablet is produced employing the same materials and procedures as in Example 8, but substituting the hemin lysinate of Example 5 for the hemin arginate.

EXAMPLE 10

A suitable composition for intravenous injection of the hemin arginate in accordance with the present invention is set forth below:

| Material | Amount (g.) |
| --- | --- |
| Hemin arginate of Example 3 | 5.24 |
| Ethanol (Spir. Fort.) | 10.50 |
| Propylene glycol | 42.00 |
| Distilled water | 105 |

EXAMPLE 11

An intravenous injection solution for hemin lysinate is formed in essentially the same proportions as set forth for hemin arginate in Example 10, except employing the hemin lysinate of Example 5 in place of the hemin arginate.

EXAMPLE 12

In order to further illustrate the superior absorption results employing the hemin arginate and hemin lysinate of the present invention, 16 healthy test subjects were treated, as indicated in Table 3 with one of hemin arginate solution, as set forth in Example 10, hemin arginate capsules having the tablet formulation of Example 8, hemin arginate capsules having the composition of Example 8 plus approximately an equal amount of vitamin C, hemin lysinate capsules having the tablet formulation set forth in Example 9, or capsules containing only hemin. In each case, the iron in the heme component was the $^{59}$Fe radioisotope to act as a tracer. The percentage of hemin iron absorbed after administration of about 4 μCi doses of each of the compositions was measured by both whole body counting and by use of a counter from the peripheral bloodstream. The doses were applied to the volunteers on either the first or second day of the test and additional testing was accomplished on each of the first through eighth days. As will be seen from the results in Table 3, the hemin arginate solution resulted in a greater iron absorption than with any of the other preparations, while all of the preparations in accordance with the present invention showed absorption of from 6 to 20 times plain hemin.

TABLE 3

| Subject No. | Product Designation | Dose (μ Ci) | 1st | 2nd | 3rd | 4th | 5th | 6th | 7th | 8th Day |
| --- | --- | --- | --- | --- | --- | --- | --- | --- | --- | --- |
| 1 | A | 3.8 | 100 | 99 | 92 | | 6.7 | 6.7 | 6.1 | |
| 2 | A | 4.3 | | 100 | 99 | 98 | 74 | 13 | | 7.9 |
| 3 | B | 4.1 | 100 | 87 | 29 | | 4.4 | 4.2 | 3.8 | |
| 4 | B | 4.0 | 100 | 91 | 55 | | 1.2 | 1.2 | 1.1 | |
| 5 | C | 4.0 | 100 | 94 | 19 | | 4.1 | 3.9 | 3.7 | |
| 6 | C | 3.4 | | 100 | 100 | 40 | 4.0 | 3.0 | | 2.5 |
| 7 | D | 3.5 | | 100 | 19 | 3.3 | 2.8 | 2.8 | | 2.5 |
| 8 | D | 4.0 | | 100 | 78 | 4.8 | 4.8 | 4.7 | | 4.4 |
| 9–16 | E | 4.0 | 100 | | | | | 0.15–0.3 | | |

A Hemin arginate solution of Example 10.
B Hemin arginate capsule with tableting formulation of Example 8.
C Hemin arginate capsule with tableting formulation plus vitamin C.
D Hemin lysinate capsule of Example 9.
E Hemin capsule.
The iron in each of the hemin materials was labeled with $^{59}$Fe.

Thus, a new material for treatment of anemia and porphyria, the new material being both stable and useful without the generation of undesired side effects, such as thrombophlebitis, has been developed. The ability to make and use the referenced materials has been illustrated in the Examples above Further, a process for producing a complex of hemin and specific amino acids has been shown and described.

Though specific embodiments of the invention have been shown and described, the invention should be considered as limited only by the appended claims

We claim:

1. A method for preparing a physiologically active, water-soluble complex of hemin and a material selected from the group consisting of L-arginine and L-lysine comprising vigorously stirring a mixture of said hemin and said material selected from the group consisting of L-arginine and L-lysine at room temperature for a period of 10 to 15 hours, the molar ratio of hemin to said material selected from the group consisting of L-arginine and L-lysine being from 1:1 to 1:4, the reaction taking place in a mixture of acetone and water which are in a ratio, on a volume basis, of from 300:10 to 300:25.

2. The method of claim 1 wherein the ratio of acetone and water is 300:20, on a volume basis.

3. The method of claim 1 wherein the molar ratio is approximately 1:3.

4. The method of claim 1 wherein the material complexed with hemin is L-arginine.

5. The method of claim 1 wherein the material complexed with hemin is L-lysine.

6. The method of claim 1 wherein the ratio of acetone to water is approximately 300:20.

7. The method of claim 1 wherein the ratio of acetone and water is 300:20, on a volume basis, and the molar ratio is approximately 1:3.

* * * * *